United States Patent
Guo et al.

(10) Patent No.: US 11,041,790 B2
(45) Date of Patent: Jun. 22, 2021

(54) STRESS GRADIENT LOADING TEST APPARATUS AND METHOD OF ACCURATELY DETERMINING LOADING ENERGY

(71) Applicant: SHANDONG UNIVERSITY OF SCIENCE AND TECHNOLOGY, Qingdao (CN)

(72) Inventors: Weiyao Guo, Qingdao (CN); Xuebin Gu, Qingdao (CN); Tongbin Zhao, Qingdao (CN); Yunliang Tan, Qingdao (CN)

(*) Notice: Subject to any disclaimer, the term of this patent is extended or adjusted under 35 U.S.C. 154(b) by 0 days.

(21) Appl. No.: 17/156,545

(22) Filed: Jan. 23, 2021

(65) Prior Publication Data
US 2021/0156775 A1 May 27, 2021

Related U.S. Application Data

(63) Continuation of application No. PCT/CN2020/082841, filed on Apr. 1, 2020.

(30) Foreign Application Priority Data

Nov. 27, 2019 (CN) .......................... 201911177665.9

(51) Int. Cl.
G01N 3/08 (2006.01)
G01N 3/06 (2006.01)
G01N 33/42 (2006.01)

(52) U.S. Cl.
CPC ............... *G01N 3/08* (2013.01); *G01N 3/066* (2013.01); *G01N 33/42* (2013.01);
(Continued)

(58) Field of Classification Search
CPC .......... G01N 3/08; G01N 3/066; G01N 33/42; G01N 2203/0617; G01N 2203/0676; G01N 2203/0019; G01N 2203/0067
See application file for complete search history.

(56) References Cited

U.S. PATENT DOCUMENTS 5,024,103 A 6/1991 Vardoulakis et al.
10,408,718 B2 * 9/2019 Zhang ...................... G01N 3/12
(Continued)

FOREIGN PATENT DOCUMENTS

CN 103969121 A 8/2014
CN 107389449 A 11/2017
(Continued)

OTHER PUBLICATIONS

Weishen et al., "Quasi-three-dimensional physical model tests on a cavern complex under high-in-situ stresses", International Journal of Rock Mechanics and Mining Sciences, vol. 48, Iss. 2, Feb. 2011, pp. 199-209, <https://www.sciencedirect.com/science/article/pii/S1365160910002108> (Year: 2011).*

(Continued)

*Primary Examiner* — Jonathan M Dunlap
(74) *Attorney, Agent, or Firm* — W&K IP

(57) ABSTRACT

The present disclosure provides a stress gradient loading test apparatus and a method of accurately determining loading energy, relating to the technical field of a rock mechanical test. The apparatus includes an upper pressure-bearing plate, a specimen fixing device, a stress transfer device, and a simulation specimen. A computer processes stress and strain monitoring data. The stress transfer device includes a plurality of plate-like high strength materials in combination. A simulation roadway is opened in the simulation specimen, and a strain gauge and a stress sensor are disposed on the simulation specimen. In a test using the apparatus, stress gradient loading is realized and elastic strain energy is calculated by the plate-like high strength materials with different stiffnesses of the stress transfer device, and loading energy acting on the simulation specimen is calculated in combination with energy applied by a tester.

2 Claims, 4 Drawing Sheets

(52) U.S. Cl.
CPC ............... *G01N 2203/0019* (2013.01); *G01N 2203/0067* (2013.01); *G01N 2203/0617* (2013.01); *G01N 2203/0676* (2013.01)

(56) References Cited

U.S. PATENT DOCUMENTS

2015/0293000 A1* 10/2015 Saussine ................. G01N 3/40
    73/82
2019/0078987 A1* 3/2019 Zhang .................... G01N 33/24

FOREIGN PATENT DOCUMENTS

| CN | 108519282 A | | 3/2018 |
|----|-------------|---|--------|
| CN | 107991184 A | | 5/2018 |
| CN | 108007781 A | | 5/2018 |
| CN | 109211668 A | * | 1/2019 |
| CN | 109632504 A | * | 4/2019 |
| CN | 110044731 A | | 7/2019 |

OTHER PUBLICATIONS

Office Action of CN201911177665.9 dated Jul. 6, 2020.
Notice of Grant Patent Right of CN201911177665.9 dated Oct. 23, 2020.
Search Report and Written Opinion of PCT/CN2020/082841, dated Jul. 30, 2021.

* cited by examiner (a)

(b)

US 11,041,790 B2

STRESS GRADIENT LOADING TEST APPARATUS AND METHOD OF ACCURATELY DETERMINING LOADING ENERGY

CROSS-REFERENCE TO RELATED APPLICATIONS

This application is a continuation of International Application No. PCT/CN2020/082841 with a filing date of Apr. 1, 2020, designating the United states, now pending, and further claim the priority of Chinese patent application 201911177665.9, filed Nov. 27, 2019. The content of the aforementioned applications, including any intervening amendments thereto, are incorporated herein by reference.

TECHNICAL FIELD

The present disclosure relates to the technical field of a rock mechanical test, in particular to a stress gradient loading test apparatus and a method of accurately determining loading energy.

BACKGROUND

A rock mechanical tester mainly includes a rock uniaxial tester and a rock triaxial tester. A rock mechanical test is one of important approaches of research in the art. The rock mechanical tester can completely simulate mechanical properties of rock soil in an initial crustal stress state. Because deep rock is in a complex stress state, it is required to research mechanical properties of rock in terms of energy for a problem of rock burst of a rock mass or an ore mass during mining engineering. The present rock mechanical tester may be applied to a rock triaxial shear test under high confining pressure, and a rock triaxial creep experiment under constant confining pressure. Test parameters may be set on request, and the entire test process is controlled with a microcomputer to record test data with a high degree of automation. However, it is difficult for the present rock mechanical tester to load a stress gradient and to apply non-uniform gradient stress loading on the same loading plane.

During a mining process, because stress on surrounding rock in underground engineering is non-uniformly distributed on each face, especially a hazardous area of rock burst, internal stress in a rock mass is easy to accumulate, and thus rock instability and failure is easier to occur. The elastic energy accumulated by the surrounding rock is quickly released to cause a rock burst dynamic disaster and influence tectonic stress and mining disturbance. Some scholars think that energy accumulation is a fundamental reason for rock burst. In different stages of rock burst, elastic energy accumulation in the early period of rock burst is greater than energy dissipation, elastic energy accumulation in the later period is smaller than energy dissipation, and the longer the early period, the larger the energy released by the rock burst. However, it is difficult for the present rock mechanical test apparatus and test method to monitor loading energy, especially difficult to determine the relationship between failure of a rock specimen and loading energy. In order to better research rock mechanical properties of the specimen in terms of energy, it is necessary to make further improvements in the present apparatus and test method.

SUMMARY

In order to realize stress gradient loading and determine energy loaded onto a simulation specimen in real time to obtain energy at failure of the specimen, the present disclosure provides a stress gradient loading test apparatus and a method of accurately determining loading energy, which specifically includes the following technical solution.

A stress gradient loading test apparatus including a rock mechanical tester, an upper pressure bearing plate, a specimen fixing device, a stress transfer device, and a simulation specimen, in which the specimen fixing device is disposed on a test bench of the rock mechanical tester, wherein the simulation specimen is placed between side baffle plates of the specimen fixing device, the stress transfer device is pressed on an upper surface of the simulation specimen, and the upper pressure bearing plate is pressed above the stress transfer device; the specimen fixing device is in a U shape, including a bottom baffle plate and two side baffle plates; the stress transfer device includes a plurality of plate-like high strength materials which are arranged in combination according to magnitude of stiffness, and the plurality of plate-like high strength materials together transfer a loading pressure of the upper pressure bearing plate; a simulation roadway is opened in the simulation specimen, a plurality of strain gauges are disposed on top and bottom plates and a side wall of the simulation roadway, and a stress sensor is disposed on an upper part of the simulation specimen; a loading system of the rock mechanical tester, the strain gauge, and the stress sensor are connected with a computer separately.

Preferably, the stress transfer device is mounted by fitting the side baffle plates of the fixing device, and a contact surface between the stress transfer device and the side baffle plate is smooth, and an indenter of the rock mechanical tester is pressed on the upper pressure bearing plate.

Preferably, the upper pressure bearing plate is a solid steel plate with a thickness smaller than a thickness of the side baffle plate of the specimen fixing device.

A method of accurately determining loading energy in a stress gradient loading test using the stress gradient loading test apparatus according to claim 1, including the following steps:

step 1. producing a simulation specimen in which a simulation roadway is opened and a strain gauge and a stress sensor are arranged;

step 2. placing a well-cured simulation specimen between the side baffle plates of the specimen fixing device;

step 3. placing the stress transfer device formed of a plurality of well-arranged plate-like high strength materials above the simulation specimen, the plurality of plate-like high strength materials are uniformly pressed on the simulation specimen, and load is applied in strip-shaped regions, in which $\sigma_i$ is a stress of each plate-like high strength material, $E_i$ is an elastic modulus of each plate-like high strength material, $\varepsilon$ is a strain of the plate-like high strength material, and i is a serial number of the plate-like high strength material which is a positive integer;

step 4. placing the upper pressure bearing plate above the stress transfer device and loading the upper pressure bearing plate by a rock mechanical tester, during the loading process:

$\sigma_i/E_i=\varepsilon$ is satisfied, and the larger the elastic modulus of the plate-like high strength material, the larger the stress transferred by the material;

step 5. calculating energy applied to the simulation specimen in a separate region, and calculating and displaying elastic strain energy of each plate-like high strength material and loading energy of the rock mechanical tester by a computer, the loading energy is converted into the elastic strain energy and the energy applied to the simulation specimen, in which the elastic strain energy can be calculated according to a formula $$U = \int_L^{\Delta 1} Pd(\Delta 1),$$

wherein P is a stress applied by the stress transfer device and monitored by the stress sensor, $\Delta l$ is a deformation amount of the simulation specimen monitored by the strain gauge; the loading energy is calculated according to a loading force F and a displacement $\Delta x$ of the indenter; and step 6. recording an energy change in a process from loading of the rock mechanical tester to failure of the simulation specimen.

The present disclosure has the following advantageous effects.

(1) In the provided stress gradient loading test apparatus, the specimen fixing device fixes the simulation specimen and is combined with the rock mechanical tester, which saves costs than directly transforming the tester. The stress transfer device uses a plurality of plate-like high strength materials with different stiffness to provide stress gradient loading according to relationships of a stress, an elastic modulus, and a strain. A simulation roadway is opened in the simulation specimen to realize simulation of a roadway and simulate relationships of energy, deformation, and failure in combination with disposition of a strain gauge.

(2) In the method of accurately determining loading energy in a stress gradient loading test, the stress gradient loading is completed by setting reasonable operation steps, the stress transfer device applies a load to the simulation specimen in strip-shaped regions, and the loading energy of the tester and the elastic strain energy of the stress transfer device are determined in accordance with the law of conservation of energy, and the energy applied to the simulation specimen can be determined in a separate region so as to realize real-time monitoring of the energy applied to the simulation specimen and finally obtain the energy at the failure of the specimen.

Figure 1:
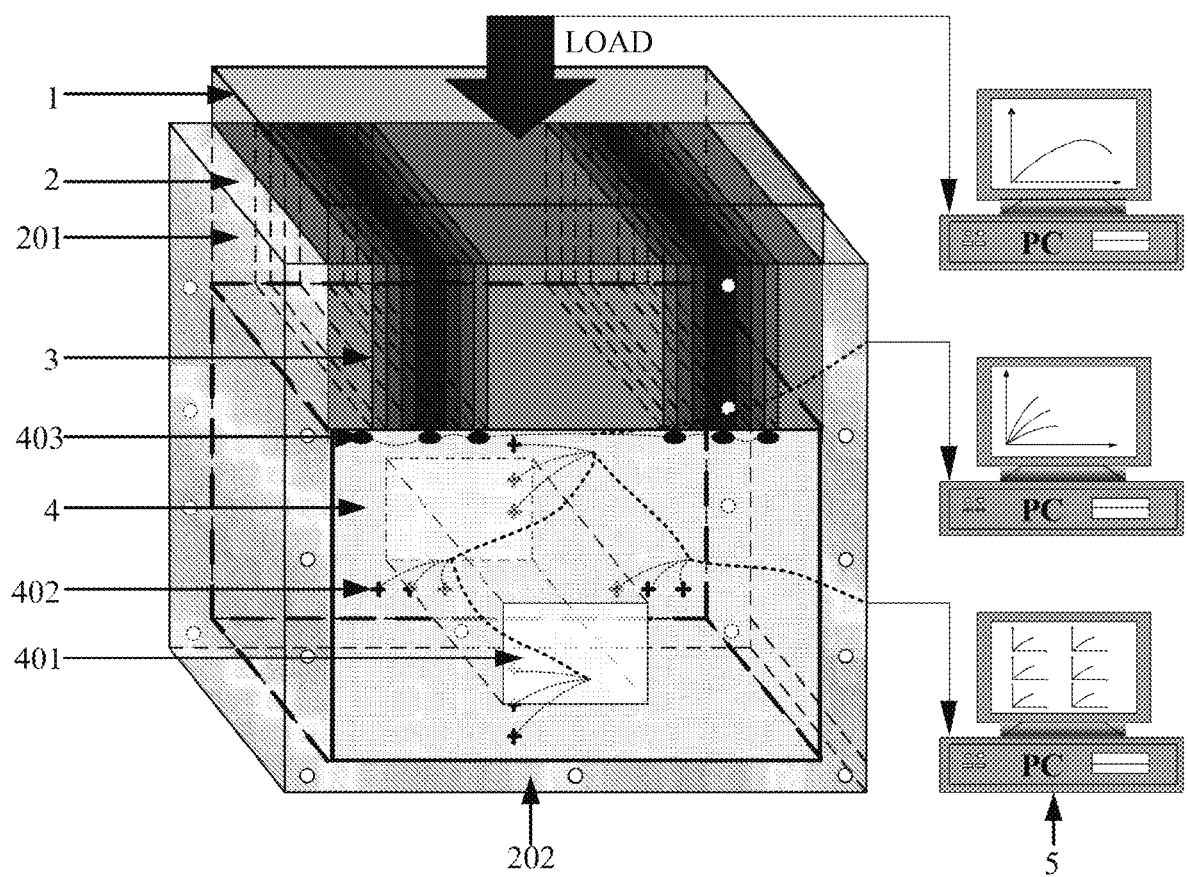
FIG. 1 is a structural schematic diagram of a loading part of a stress gradient loading test apparatus.
Figure 2:
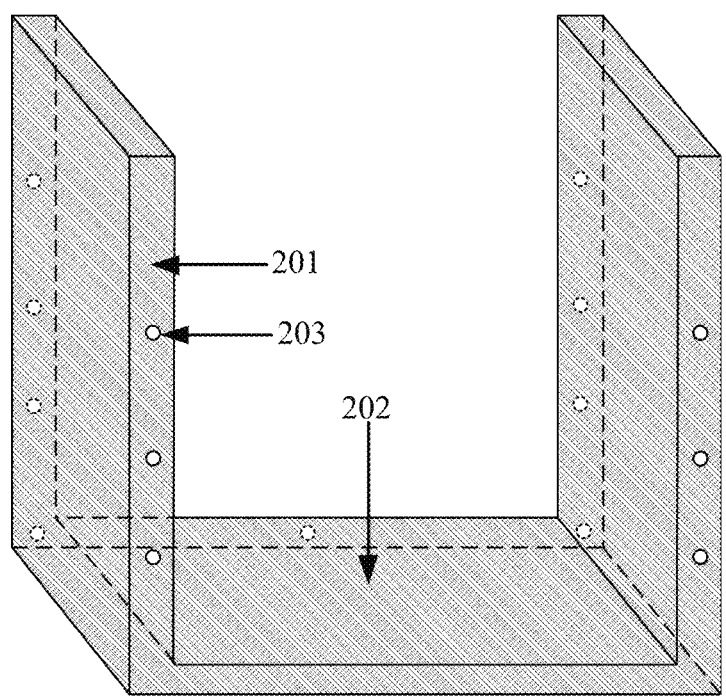
FIG. 2 is a structural schematic diagram of a specimen fixing device.
Figure 3:
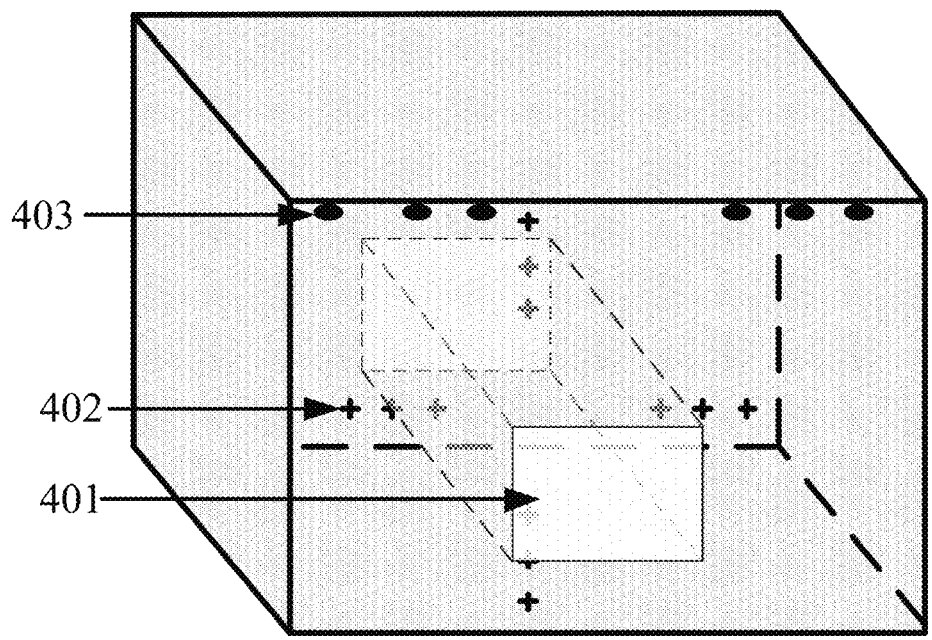
FIG. 3 is a structural schematic diagram of a simulation specimen.

Reference numerals in the drawings are as follows: 1. upper pressure bearing plat; 2. specimen fixing device; 3. stress transfer device; 4. simulation specimen; 5. computer; 6. rock tester; 7. test bench of rock tester; 201. side baffle plate; 202. bottom baffle plate; 203. screw hole; 401. simulation roadway; 402. strain gauge; 403. stress sensor; 404. stress distribution curve.

DETAILED DESCRIPTION OF EMBODIMENTS

As shown in FIGS. 1 to 5, the present disclosure provides a stress gradient loading test apparatus and a method of accurately determining loading energy, which specifically includes the following technical solution.

A specific structure of a stress gradient loading test apparatus includes a rock mechanical tester, an upper pressure bearing plate, a specimen fixing device, a stress transfer device, and a simulation specimen. The specimen fixing device is disposed on a test bench of the rock mechanical tester which can be a normal uniaxial compression tester. The specimen fixing device and the rock mechanical tester are detachably mounted on each other. In the stress gradient loading test apparatus, the specimen fixing device fixes the simulation specimen and is combined with the rock mechanical tester, which saves costs than directly transforming the tester. The stress transfer device uses a plurality of plate-like high strength materials with different stiffness to provide stress gradient loading according to relationships of a stress, an elastic modulus, and a strain. A simulation roadway is opened in the simulation specimen to realize simulation of a roadway and simulate relationships of energy, deformation, and failure in combination with disposition of a strain gauge.

The simulation specimen is placed between the side baffle plates of the specimen fixing device so that a negligible tiny fit clearance is left therebetween. A plurality of screw holes are disposed on a side face of the specimen fixing device. A baffle plate may be added at front and rear ends of the side baffle plate as required. The stress transfer device is pressed on an upper surface of the simulation specimen which is a smooth and flat contact surface. The upper pressure-bearing plate which is stiff plate is pressed on the stress transfer device. The upper pressure bearing plate and the side baffle plate of the specimen fixing device fit each other, and a width between the side baffle plates is slightly greater than a width of the upper pressure bearing plate. The specimen fixing device is in a U shape and includes a bottom baffle plate and two side baffle plates. The stress transfer device includes a plurality of plate-like high strength materials which are arranged in combination according to magnitude of stiffness. The plurality of plate-like high strength materials jointly transfer a loading pressure of the upper pressure bearing plate. The stress transfer device is mounted by fitting the side baffle plates of the fixing device, and a contact surface between the stress transfer device and the side baffle plate is smooth. An indenter of the rock mechanical tester is pressed on the upper pressure bearing plate. The upper pressure bearing plate is a solid steel plate with a thickness smaller than a thickness of the side baffle plate of the specimen fixing device.

A simulation roadway is opened in the simulation specimen, and the size and shape of the roadway are determined according to a test scale. The simulation specimen may be made of similar materials, and a plurality of strain gauges are disposed on top and bottom plates and a side wall of the simulation roadway to monitor simulated deformations of the top plate, the bottom plate, the side wall, and their accessories of the simulation roadway. Stress sensors are disposed above the simulation specimen to monitor a stress applied to the simulation specimen and cause the numbers of the plate-like high strength materials and the stress sensors to match each other, thereby determining a force applied by each plate-like high strength material to the simulation specimen. A loading system of the rock mechanical tester, the strain gauge, and the stress sensor are connected with a computer separately.

A method of accurately determining loading energy in a stress gradient loading test using the above stress gradient loading test apparatus includes the following steps.

Step 1. Producing a simulation specimen in which a simulation roadway is opened and a strain gauge and a stress sensor are arranged, in which a process of producing the simulation specimen includes: preparing similar materials; determining the size of the simulation specimen; and directly leaving a simulation roadway by mold casting or preparing a cubic specimen and digging a simulation roadway therein, and during the process of producing the simulation specimen, the strain gauge and the stress sensor are reasonably fixed in the simulation specimen.

Step 2. Placing a well-cured simulation specimen between the side baffle plates of the specimen fixing device. After solidification, the simulation specimen is well cured, and a surface of the specimen is polished smooth, especially an upper surface of the simulation specimen needs to be flat and smooth.

Step 3. Placing the stress transfer device formed of a plurality of well-arranged plate-like high strength materials above the simulation specimen, the plurality of plate-like high strength materials are uniformly pressed on the simulation specimen, and load is applied in strip-shaped regions. $\sigma_i$ is a stress of each plate-like high strength material, $E_i$ is an elastic modulus of each plate-like high strength material, $\varepsilon$ is a strain of the plate-like high strength material, and i is a serial number of the plate-like high strength material which is a positive integer.

Figure 4:
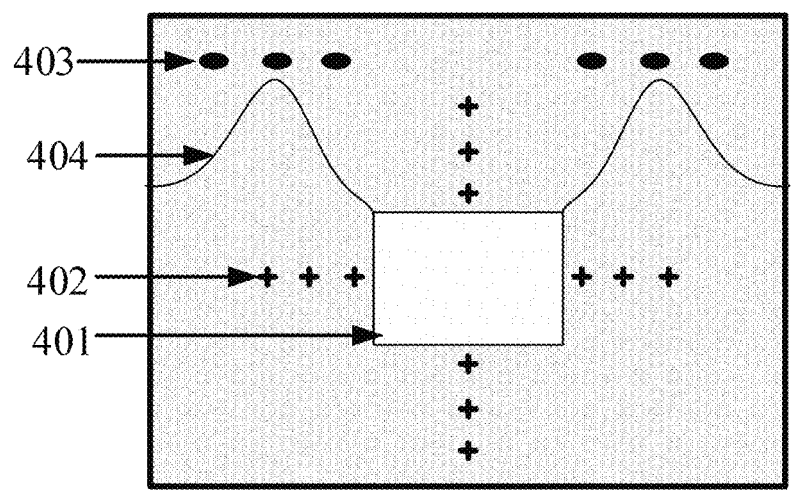
FIG. 4 is a schematic diagram of a cross section and a stress distribution curve of the simulation specimen.
Figure 4:
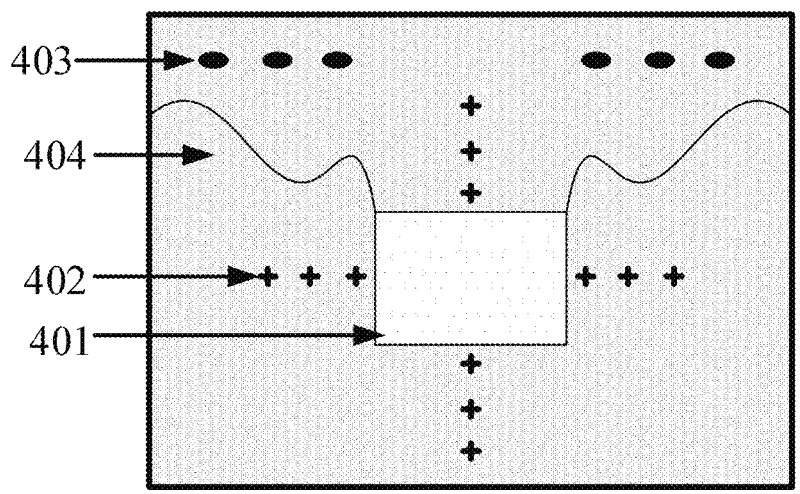
Figure 5:
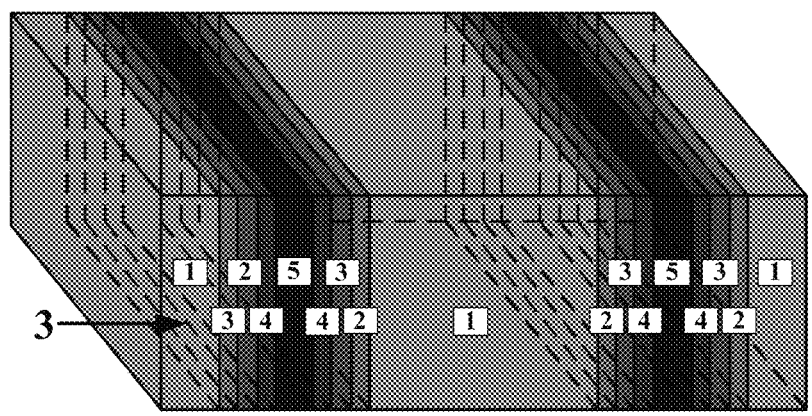
FIG. 5 is a structural schematic diagram of a stress transfer device.
Figure 6:
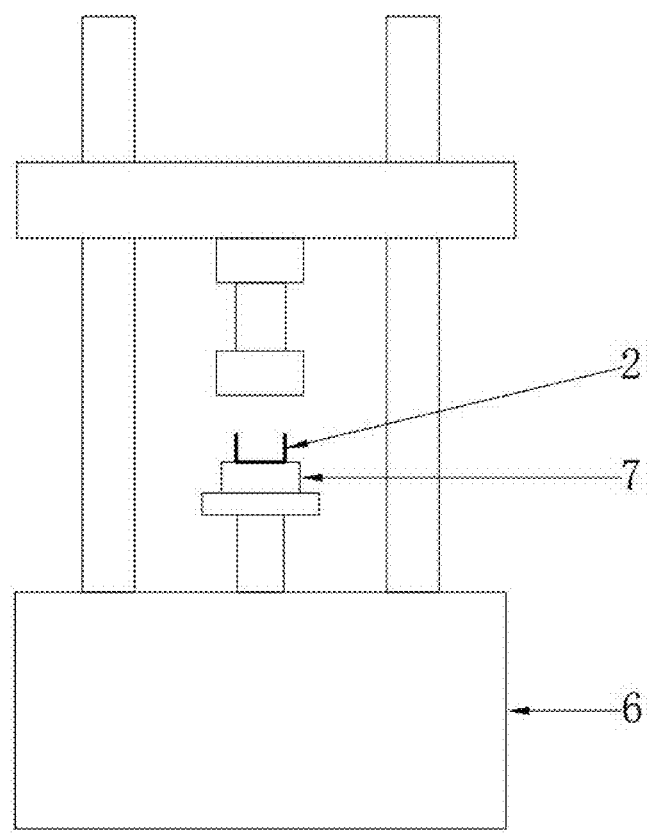
FIG. 6 is a structural schematic diagram of a rock tester and a test bench.

As shown in FIG. 4, by changing a distribution of plate-like high strength materials with different elastic moduli, different stress distribution curves may be set to simulate a stress state of surrounding rock of the simulation roadway. As shown in FIG. 5, the plate-like high strength materials may be numbered according to magnitude of elastic moduli thereof or numbered sequentially as arranged. FIG. 5 shows numbering performed according to the elastic moduli of the materials. Plate-like high strength materials with equal elastic moduli are assigned the same number, and widths of the plate-like high strength materials may be equal or unequal. According to actual test need, a plate-like high strength material with a larger elastic modulus is selected in a region to which a larger stress needs to be applied, and a plate-like high strength material with a smaller elastic modulus is selected in a region to which a smaller stress needs to be applied. The "larger" and "smaller" specifically refer to comparison of the elastic moduli of the plate-like high strength materials. Elastic moduli of the adjacent plate-like high strength materials at both sides of a stress peak position diminish sequentially so that loading conforms more to an actual crustal stress distribution.

Step 4. Placing the upper pressure bearing plate above the stress transfer device and loading the upper pressure bearing plate by a rock mechanical tester. During the loading process:

$\sigma_i/E_i=\varepsilon$ is satisfied, and the larger the elastic modulus of the plate-like high strength material, the larger the stress transferred by the material.

During the loading process, strains of different combinations of the plate-like high strength materials are equal. Therefore, selection of a combined plate at each position of the stress transfer device may be calculated according to the following formula:

$\sigma_1/E_1=\sigma_2/E_2=\sigma_3/E_3=\sigma_4/E_5=\varepsilon$ wherein i=1, 2, 3, 4, 5, which correspond to serial numbers in FIG. 5 and represent plate-like high strength materials with different stiffness. It can be known from the above formula that the larger the stiffness (elastic modulus E) of each plate-like high strength material, the larger the stress transferred by the material under the same strain. That is, a stress loading gradient can be realized by adjusting stiffness of the combined plate.

Step 5. Calculating energy applied to the simulation specimen in a separate region, and calculating and displaying elastic strain energy of each plate-like high strength material and loading energy of the rock mechanical tester by a computer; the loading energy is converted into the elastic strain energy and the energy applied to the simulation specimen.

The elastic strain energy can be calculated according to a formula $$U = \int_L^{\Delta l} Pd(\Delta l),$$

wherein P is a stress applied by the stress transfer device and monitored by the stress sensor, $\Delta l$ is a deformation amount of the simulation specimen monitored by the strain gauge; the loading energy is calculated according to a loading force F and a displacement $\Delta x$ of the indenter.

A calculation principle of the loading energy is as follows: slowly applying an external force to an object does not cause the object to generate an acceleration, which can be regarded as that energy applied by the external force is all converted into strain energy and stored in the object, that is, energy transferred by the stress transfer device is all converted into the elastic strain energy of the specimen, and corresponding elastic strain energy applied by the stress transfer device is obtained by the elastic strain energy calculation formula. In the formula, $\Delta l$ is a displacement and can be monitored by the strain gauge; P is a force applied by the stress transfer device. In accordance with Newton's third law, action of a force is mutual. Therefore, the force P may be monitored by the stress sensor or calculated according to the strain $\varepsilon$ recorded by the elastic modulus of the stress transfer device and the displacement of the loading device, and then the energy applied to the specimen may be calculated in a separate region by the elastic strain energy calculation formula.

A calculation principle of specimen failure energy is as follows: the energy applied by the rock mechanical tester is converted into two parts: one part is loaded onto the specimen and finally causes failure of the specimen; the other part is stored in the stress transfer device in a form of elastic strain energy. The energy stored in the stress transfer device can be calculated by the elastic strain energy calculation formula; the energy loaded onto the specimen can be calculated by the loading force F and the displacement $\Delta x$. Energy at failure of the specimen is calculated using data collected immediately after the failure of the specimen.

The calculation principle of the above energy is as follows: by collecting, calculating, and processing data with a computer, real-time energy calculation and display can be realized during the loading process.

Step 6. Recording an energy change in a process from loading of the rock mechanical tester to failure of the simulation specimen.

The upper pressure bearing plate is loaded by the indenter of the rock mechanical tester, and test data during the loading process is recorded and exported by a computer; test data is recorded during the loading process and displayed in real time by a computer.

The stress state of rock corresponds to an energy state of rock, and energy exchanges all along during a failure process of rock including an elastic stage, a yield stage, and a failure stage. Therefore, by accurately obtaining energy of a rock specimen at each stage, a rock failure strength theory close to reality can be established to obtain a more accurate rock failure law.

Compared with other stress loading devices, stress gradient loading can be ensured using high strength materials, and loading energy can be accurately determined by the disposed strain gauge, stress transfer device, and the like. The above test method is easy and convenient to operate and brings accurate measurement, thereby well satisfying requirements of a rock specimen loading test.

Of course, the above descriptions are not intended to limit the present disclosure. The present disclosure is not limited to the above examples. Variations, modifications, additions, or substitutions made by those skilled in the art within the essential scope of the present disclosure shall all fall within the scope of protection of the present disclosure.

We claim:

1. A stress gradient loading test apparatus comprising a rock mechanical tester, an upper pressure bearing plate, a specimen fixing device, a stress transfer device, and a simulation specimen, in which the specimen fixing device is disposed on a test bench of the rock mechanical tester, wherein the simulation specimen is placed between side baffle plates of the specimen fixing device, the stress transfer device is pressed on an upper surface of the simulation specimen, and the upper pressure bearing plate is pressed above the stress transfer device; the specimen fixing device is in a U shape, including a bottom baffle plate and two side baffle plates; the stress transfer device includes a plurality of plate-like high strength materials which are arranged in combination according to magnitude of stiffness, and the plurality of plate-like high strength materials together transfer a loading pressure of the upper pressure bearing plate; a simulation roadway is opened in the simulation specimen, a plurality of strain gauges are disposed on top and bottom plates and a side wall of the simulation roadway, and a stress sensor is disposed on an upper part of the simulation specimen; a loading system of the rock mechanical tester, the strain gauge, and the stress sensor are connected with a computer separately; the stress transfer device is mounted by fitting the side baffle plates of the fixing device, and a contact surface between the stress transfer device and the side baffle plate is smooth, and an indenter of the rock mechanical tester is pressed on the upper pressure bearing plate; and the upper pressure bearing plate is a solid steel plate with a thickness smaller than a thickness of the side baffle plate of the specimen fixing device.

2. A method of accurately determining loading energy in a stress gradient loading test using the stress gradient loading test apparatus according to claim 1, comprising the following steps:

step 1. producing a simulation specimen in which a simulation roadway is opened and a strain gauge and a stress sensor are arranged;

step 2. placing a well-cured simulation specimen between the side baffle plates of the specimen fixing device;

step 3. placing the stress transfer device formed of a plurality of well-arranged plate-like high strength materials above the simulation specimen, the plurality of plate-like high strength materials are uniformly pressed on the simulation specimen, and load is applied in strip-shaped regions, in which $\sigma_i$ is a stress of each plate-like high strength material, $E_i$ is an elastic modulus of each plate-like high strength material, $\varepsilon$ is a strain of the plate-like high strength material, and i is a serial number of the plate-like high strength material which is a positive integer;

step 4. placing the upper pressure bearing plate above the stress transfer device and loading the upper pressure bearing plate by a rock mechanical tester, during the loading process:

$\sigma_i/E_i=\varepsilon$ is satisfied, and the larger the elastic modulus of the plate-like high strength material, the larger the stress transferred by the material;

step 5. calculating energy applied to the simulation specimen in a separate region, and calculating and displaying elastic strain energy of each plate-like high strength material and loading energy of the rock mechanical tester by a computer; the loading energy is converted into the elastic strain energy and the energy applied to the simulation specimen, in which the elastic strain energy can be calculated according to a formula $$U = \int_{L}^{\Delta l} P d(\Delta l),$$

wherein P is a stress applied by the stress transfer device and monitored by the stress sensor, $\Delta l$ is a deformation amount of the simulation specimen monitored by the strain gauge; the loading energy is calculated according to a loading force F and a displacement $\Delta x$ of the indenter; and step 6. recording an energy change in a process from loading of the rock mechanical tester to failure of the simulation specimen.

* * * * *